US008110407B2

(12) United States Patent
Tsukada et al.

(10) Patent No.: US 8,110,407 B2
(45) Date of Patent: Feb. 7, 2012

(54) FLUORESCENT SEMICONDUCTOR MICROPARTICLE ASSEMBLY, FLUORESCENT LABELING AGENT ASSEMBLY FOR BIOLOGICAL SUBSTANCE, AND BIOIMAGING METHOD AND BIOLOGICAL SUBSTANCE ANALYSIS METHOD USING THE ASSEMBLIES

(75) Inventors: Kazuya Tsukada, Kanagawa (JP); Hisatake Okada, Tokyo (JP); Hideki Hoshino, Tokyo (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 305 days.

(21) Appl. No.: 12/440,421

(22) PCT Filed: Aug. 22, 2007

(86) PCT No.: PCT/JP2007/066256
§ 371 (c)(1),
(2), (4) Date: Mar. 6, 2009

(87) PCT Pub. No.: WO2008/032534
PCT Pub. Date: Mar. 20, 2008

(65) Prior Publication Data
US 2010/0041017 A1   Feb. 18, 2010

(30) Foreign Application Priority Data

Sep. 14, 2006   (JP) .................................. 2006-249208

(51) Int. Cl.
*G01N 33/543*   (2006.01)
*G01N 21/76*   (2006.01)
(52) U.S. Cl. ........ 436/523; 436/518; 436/524; 436/528; 436/534; 436/10; 436/172; 422/82.08
(58) Field of Classification Search .................. 435/2, 6, 435/172; 436/501, 546, 518, 523, 524, 528, 436/534, 10, 172; 250/302, 307, 459.1; 422/82.08
See application file for complete search history.

(56) References Cited

U.S. PATENT DOCUMENTS

| 6,630,307 B2 * | 10/2003 | Bruchez et al. .................. 435/6 |
| 2006/0140240 A1 | 6/2006 | Chen | |

FOREIGN PATENT DOCUMENTS

| EP | 1978366 | 10/2008 |
| JP | 62116264 | 5/1987 |
| JP | 2002311027 | 10/2002 |
| JP | 2005508493 | 3/2005 |
| JP | 2005172429 | 6/2005 |
| JP | 2005189237 | 7/2005 |
| JP | 2006162284 | 6/2006 |
| WO | 03075765 | 9/2003 |
| WO | 2005003380 | 1/2005 |
| WO | 2005017525 | 2/2005 |

OTHER PUBLICATIONS

Holmes J D et al: "Highly luminescent silicon nanocrystals with discrete optical transitions" Journal of the American Chemical Society 2001 American Chemical Society US, vol. 123, No. 16, 2001, pp. 3743-3748, XP002594953 DOI: DOI:10.1021/JA002956F *abstract* *figures 10-12*.

Belomoin G et al: "Observation of a magic discrete family of ultrabright Si nanoparticles" Applied Physics Letters, AIP, American Institute of Physics, Melville, NY, US LNKD-DOI: 10.1063/1. 1435802, vol. 80, No. 5, Feb. 4, 2002, pp. 841-843, XP012031470, ISSN: 0003-6951*p. 841, right-hand column, paragraph 3- p. 842, right-hand column, paragraph 2; figures 2,3**p. 843, right-hand column, paragraph 2.

Peng X et al: "Epitaxial growth of highly luminescent CdSe/CdS core/shell nanocrystals with photostability and electronic accessibility", Journal of the American Chemical Society, American Chemical Society, New York, US, LNKD-DOI:10, 1021/JA970754M, vol. 119, Jan. 1, 1997, pp. 7019-7029, XP002261067, ISSN: 0002-7863 *figure 4* .

Mingyong Han et al: "Quantum-dot-tagged microbeads for multiplexed optical coding of biomolecules" Nature Biotechnology, Nature Publishing Group, New York, NY, US LNKD-DOI:10.1038/ 90228, vol. 19, No. 7, Jul. 1, 2001, pp. 631-635, XP 002545495, ISSN: 1087-0156 *p. 632, right-hand column, paragraph 3- p. 634, right-hand column, paragraph 3; figures 1-4*.

Hanaki K et al: "Semiconductor Quantum DOT/Albumin Complex is a Long-Life and Highly Photostable Endosome Marker", Biochemical and Biophysical Research Communications, Academic Press, Inc. Orlando, FL. US LNKD-DOI: 10.1016/S0006-291X(03)00211-0, vol. 302, No. 3, Jan. 1, 2003, pp. 496-501, XP008053309, ISSN: 0006-291X, *the whole document.

Fujii Minoru et al: "Breakdown of the k-conservation rule in Sil-xGex alloy nanocrystals: Resonant photoluminescence study", Journal of Applied Physics, American Institute of Physics. New York, US LNKD-DOI:10.1063/1.1319969, vol. 88, No. 10, Nov. 15, 2000, pp. 5772-5776, XP012050893 ISSN: 0021-8979 *the whole document*.

Supplemental European Search Report EP 07 79 2854 (10 pages).

Kazunari Yamana, "Handotai Nano Biryushi o Riyo shita Seitai Bunshi no Keiko Label", Chemistry, vol. 55, No. 1, pp. 72 to 73, full text, (1987).

Norio Murase, "Kosoku Daiyoryoka ni Taio suru Kogaku Zairyo Kokido Display-yo Nano Glass Keikotai", Kogyo Zairyo, vol. 51, No. 8, 2003, pp. 66 to 69.

Shiho Katsukawa, "Atarashii Seitai Bunshi no Multi Color Label Gijutsu", Chemistry & chemical industry, vol. 55, No. 9, 2002, p. 1029, full text.

Takeo Ito, "Saishin Keiko Imaging Katsuyojutsu Dai 8 Kai Quantum dot o Mochiita live cell Kansatsu—Kyoshoten Laser Kenbikyo ni yoru Yojigen Spectrum Kaiseki-", Bio Technology Journal, vol. 6, No. 4, Jul. 1, 2006, pp. 487 to 493, full text.

\* cited by examiner

*Primary Examiner* — Gail R Gabel
(74) *Attorney, Agent, or Firm* — Lucas & Mercanti, LLP

(57) ABSTRACT

Disclosed is a fluorescent semiconductor microparticle assembly comprising at least three kinds of fluorescent semiconductor microparticles with an average particle size of from 1 to 10 nm, having the same chemical composition, a different average particle size and a different emission maximum wavelength in the emission spectra, wherein a standard deviation of emission intensity in each of the at least three kinds of fluorescent semiconductor microparticles is not more than 15%.

4 Claims, No Drawings

FLUORESCENT SEMICONDUCTOR MICROPARTICLE ASSEMBLY, FLUORESCENT LABELING AGENT ASSEMBLY FOR BIOLOGICAL SUBSTANCE, AND BIOIMAGING METHOD AND BIOLOGICAL SUBSTANCE ANALYSIS METHOD USING THE ASSEMBLIES

This is a U.S. National Phase Application under 35 U.S.C. 371 of International Application PCT/JP2007/066256, filed on Aug. 22, 2007, which claims the priority of Japanese Application No. 2006-249208, filed Sep. 14, 2006, the entire content of both Applications are hereby incorporated by reference.

FIELD OF THE INVENTION

The present invention relates to a fluorescent semiconductor microparticle assembly, fluorescent labeling agent assembly for a biological substance, and a bioimaging method and a biological substance analysis method using the assemblies.

Particularly, the present invention relates to a fluorescent labeling agent assembly for a biological substance, the assembly comprised of at least three kinds of fluorescent semiconductor microparticles having a different particle size, a different wavelength of emission maximum in the emission spectra, and substantially the same emission intensity. Further, the present invention relates to a fluorescent labeling agent assembly for a biological substance, which is useful for biology in which kinetic analysis of cells is carried out or for dynamic imaging in the immunity analysis fields and to a bioimaging or flow cytometry method using the assembly.

TECHNICAL BACKGROUND

In recent years, an active study has been made of semiconductor nanoparticles capable of controlling the fluorescent wavelength due to the different particle size. The semiconductor nanoparticles have been studied and utilized as fluorescent markers labeled inside or outside of a living organism, since they have controllability of the fluorescent wavelength, high light fastness and high surface modification freedom (see for example, Patent Documents 1 through 3 described later).

Particularly in recent years, there has been actively made a fundamental medical study, in which analysis of reaction mechanism of living molecules within living cells is shifted from qualitative assay in a bulk living organism analysis to kinetic analysis at molecule level, or a study on bioimaging, in which biological action of viruses or bacteria causing diseases, or biological action of medicines is analyzed. Particularly, as is represented by molecular imaging, information (dynamics from DNA transfer mRNA to protein formation, cell apoptosis dynamics, etc.) regarding a biological substance, which has not been obtained hitherto, is obtained by conjugating one molecule of a biological substance to be detected (nucleuses within cells, endoplasmic reticulum, Golgi body, proteins, DNA, RNA) with one or several molecules of a fluorescent labeling agent, irradiating the conjugate with an excitation light, and detecting the emission light. When target substances within living organisms such as living cells or small animals are traced, qualitatively or quantitatively analyzed, it is desired that the plural target substances can be simultaneously analyzed. Trace due to simultaneous marking is essential in order to analyze mechanisms such as a biological mechanism in which plural molecules within cells participate, a developing mechanism of viruses, and endocytosis.

However, organic fluorescent dyes or fluorescent proteins hitherto used as markers are small in Stokes shift which is the difference in wavelength between excitation light and emission light and the different organic fluorescent dyes are necessary to be irradiated with an excitation light suitable for each of the organic fluorescent dyes Therefore, when simultaneous multi (many or many kinds) analysis is carried out, excitation light sources equal to the number of markers are required, resulting in complexity and cost increase of an analysis device, an excitation-fluorescent light separation filter, which is necessary on account of small stokes shift, inhibits its fluorescence from other markers in the plural markers, and plural excitation lights result in fluorescence noise. Thus, multi analysis has been difficult (see for example, Patent Document 4 described later).

With respect to kinetic analysis of molecules, which has been actively studied in fundamental medical areas, it is pointed out that emission intensity to be detected per one sample is poor and its discrimination accuracy in multi analysis is low. Accordingly, further improvement in discrimination accuracy has been desired.

In order to solve the above problems regarding the multi analysis, it is necessary to manufacture semiconductor quantum size particles with high accuracy and in a number necessary to multi analysis, the particles exhibiting quantum effects that are different in emission wavelength according to the different particle size. However, this manufacture itself is difficult.

Patent Document 1; Japanese Patent O.P.I. Publication No. 2003-329686
Patent Document 2: Japanese Patent O.P.I. Publication No. 2005-172429
Patent Document 3: Japanese Translation of PCT International Application Publication No. 2003-524147
Patent Document 4: Japanese Patent O.P.I. Publication No. 2003-287498

DISCLOSURE OF THE INVENTION

Problems to be Solved by the Invention

The present invention has been made in view of the above. The present invention is to provide a fluorescent semiconductor microparticle assembly realizing dynamic imaging with high accuracy simultaneously detecting (multi-detecting) at least three kinds of targets, its manufacturing method, a fluorescent labeling agent assembly for a biological substance using the microparticle assembly, and an imaging or flow cytometry method using the microparticle assembly.

Means for Solving the Above Problems

The above problems in the invention can be solved by any one of the following constitutions.

1. A fluorescent semiconductor microparticle assembly comprising at least three kinds of fluorescent semiconductor microparticles with a particle size of from 1 to 10 nm, having the same chemical composition, a different particle size and a different emission maximum wavelength in the emission spectra, characterized in that a standard deviation of emission intensity in each of the at least three kinds of fluorescent semiconductor microparticles is not more than 15%.

2. The fluorescent semiconductor microparticle assembly of item 1 above, characterized in that the wavelength of emission maximum in the emission spectra is in the range of from 380 to 800 nm.

3. The fluorescent semiconductor microparticle assembly of item 1 or 2 above, characterized in that the at least three kinds of fluorescent semiconductor microparticles having a different emission maximum wavelength in the emission spectra emit light on irradiation with one kind of excitation light.

4. A method of manufacturing the fluorescent semiconductor microparticle assembly of any one of items 1 through 3 above, characterized in that the fluorescent semiconductor microparticles are manufactured according to a liquid phase method.

5. A fluorescent labeling agent assembly for a biological substance, characterized in that the fluorescent semiconductor microparticles, constituting the fluorescent semiconductor microparticle assembly of any one of items 1 through 4, have on the surface a surface-modifying compound having a functional group through which is associated with a biological substance and a functional group through which is associated with the fluorescent semiconductor microparticle surface.

6. The fluorescent labeling agent assembly for a biological substance of item 5 above, characterized in that the fluorescent semiconductor microparticles having a different particle size, constituting the fluorescent semiconductor microparticle assembly of any one of items 1 through 4 above, have on the surface a different surface-modifying compound suitable for a different biological substance.

7. A bioimaging method characterized in that fluorescent dynamic imaging of at least three kinds of target or trace substances is simultaneously carried out employing the fluorescent labeling agent assembly for a biological substance of item 5 or 6 above.

8. A biological substance analysis method characterized in that multi-flow cytometry of a biological substance is carried out, employing polymer beads in which the fluorescent semiconductor microparticle assembly of any one of items 1 through 3 above is buried.

Effect of the Invention

The present invention can provide a fluorescent semiconductor microparticle assembly realizing dynamic imaging with high accuracy simultaneously detecting (multi-detecting) at least three kinds of targets, its manufacturing method, a fluorescent labeling agent assembly for a biological substance using the microparticle assembly, and an imaging or flow cytometry method using the microparticle assembly.

The present invention can provide a highly sensitive and accurate measurement method particularly in the research field of single molecule imaging.

PREFERRED EMBODIMENT OF THE INVENTION

Next, the invention and the constituents of the invention will be explained in detail.
(Fluorescent Semiconductor Microparticle Assembly)

The fluorescent semiconductor microparticle assembly of the invention comprises at least three kinds of fluorescent semiconductor microparticles with a particle size of from 1 to 10 nm having the same chemical composition, a different particle size and a different wavelength of emission maximum in the emission spectra, wherein the standard deviation of the emission intensities of the fluorescent semiconductor microparticles is not more than 15%.

Herein, "the fluorescent semiconductor microparticle assembly" means one used for testing one living organism, which comprises plural fluorescent semiconductor microparticle species with a particle size of from 1 to 10 nm having a different average particle size. Each microparticle species having a specific particle size in the assembly is employed as a labeling agent for one biological substance, and at the same time plural biological substances are tested in one test. The assembly can be used in plural separate beads. Further, beads in which the fluorescent semiconductor microparticles are buried, modified to have affinity to a biological substance, can be used as a label agent.

The average particle size of the fluorescent semiconductor microparticles in the invention is from 1 to 10 nm. When the microparticles have a core/shell structure, the average particle size of the microparticles means that of the core. The particle size distribution of each of the fluorescent semiconductor microparticle species having a different average particle size is preferably monodisperse, and the standard deviation in the particle size distribution is preferably not more than 20%, and more preferably not more than 10%.

It is required that each of the fluorescent semiconductor microparticles having a different particle size, constituting the fluorescent semiconductor microparticle assembly, has uniformity such that the standard deviation of the emission intensities is not more than 15%. When the emission intensities greatly vary, emission with lower emission intensities are healed by higher ones, resulting in lowering of discrimination property and accuracy.

It is required that in the fluorescent semiconductor microparticles in the invention, the emission maximum wavelength in the emission spectra is from 380 to 800 nm The reason that the emission maximum wavelength includes infrared and near-infrared regions is because there are advantages in that the multi number can be increased and light having a high transmission capability makes it possible to detect biological substances which are present in positions deep within an living organism.

It is preferred that the at least three fluorescent semiconductor microparticles having a different emission maximum wavelength in the emission spectra emit light on irradiation with one kind of excitation light (which may have a single wavelength or plural wavelengths). That is, it is preferred that the fluorescent semiconductor microparticles emit light on irradiation with one kind of excitation light from one excitation light source. There are advantages that one excitation light source makes it possible to simplify a detector, requires no extra filter, and further enables easy detection or observation, which can more effectively exhibit the advantages of the invention.

As a method for realizing each of the fluorescent semiconductor microparticle species in the invention having the same composition and having a uniform emission intensity wherein the standard deviation of the emission intensities is not more than 15%, there is one in which increasing crystallinity of the fluorescent semiconductor microparticles and controlling the inner and surface defects of the fluorescent semiconductor microparticles. The microparticles with a larger particle size, in which the surface area per particle is large and the particle number is less, have a great influence on light emission per one particle. Therefore, such microparticles with a larger particle size require a technique for reducing the defects as compared with those having a smaller particle size (a technique as described later which optimizes purity of law materials, synthesis concentration, synthesis temperature and times and an annealing temperature and time after particle formation in the fluorescent semiconductor microparticle manufacturing process). The present invention can be attained by employing optimum synthesis conditions and the technique as above regarding each of the fluorescent semiconductor microparticles.

<Materials for Fluorescent Semiconductor Microparticles>

The fluorescent semiconductor microparticles constituting the fluorescent semiconductor microparticle assembly of the invention can be prepared employing various semiconductor materials. Examples thereof include semiconductor materials comprising Group IV elements, elements of Groups II and VI and elements of Groups III and V of the periodic table.

Examples of the semiconductor materials comprising elements of Groups II and VI include MgS, MgSe, MgSe, MgTe, CaS, CaSe, CaTe, SrS, SrSe, SrTe, BaS, BaSe, BaTe, ZnS, ZnSe, ZnTe, CdS, CdSe, HgS, HgSe, and HgTe.

Examples of the semiconductor materials comprising elements of Groups III and V include GaAs, GaN, GaPGaSb, InGaAs, InP, InN, InSb, InAs, AlAs, AlP, AlSb, and AlS.

Examples of the semiconductor materials comprising Group IV elements include Ge, Pb and Si.

In the invention, the fluorescent semiconductor microparticles are preferably ones having a core/shell structure. The fluorescent semiconductor microparticles are ones having a core/shell structure which comprises a core comprised of the fluorescent semiconductor microparticles covered with a shell. It is preferred that the chemical composition of the core is different from that of the shell.

Next, the core and the shell will be explained.

<Core>

Examples of the semiconductor material for the care include MgS, MgSe, MgTe, CaS, CaSe, CaTe, SrS, SrSe, SrTe, BaS, BaTe, ZnS, ZnSe, ZnTe, CdS, CdSe, CdTe, GaAs, GaP, GaSb, InGaAs, InP, InN, InSb, InAs, AlAs, AlP, AlSb, AlS, PbS, PbSe, Ge, Si, and an admixture thereof. In the invention, Si is especially preferred.

A dope material such as Ga may be contained in a small amount as necessary.

It is required that the average particle size of the core in the invention is from 1 to 10 nm in effectively exhibiting the effects of the invention. The core with an average particle size of 1 to 10 nm enables labeling and detecting of a bio-molecule with a small particle size. Further, the core with an average particle size of from 1 to 5 nm enables labeling and dynamic imaging of a bio-molecule with a small particle size. Accordingly, it is especially preferred that the average particle size of the core is from 1 to 5 nm.

The average particle size of the core in the invention implies a particle size of a cumulative volume of 50%, measured through a laser scattering method.

<Shell>

Various semiconductor materials can be used as semiconductor materials used in the shell. Typical examples of the semiconductor materials include ZnO, ZnS, ZnSe, ZnTe, CdO, CdS, CdSe, CdTe, MgS, MgSe, GaS, GaN, GaP, GaAs, GaSb, InAs, InN, InP, InSb, AlAs, AlN, aluminum plate and AlSb.

As preferred semiconductor materials for the shell, there are semiconducting materials having a bandgap energy greater than a semiconductor nanocrystal core In addition to having a bandgap energy greater than the semiconductor nanocrystal core, suitable materials for the shell should have good conductivity and valence band offset regarding the core semiconductor nanocrystal. Accordingly, the conduction band is preferably higher than that of the core semiconductor nanocrystal, and the valence band is preferably lower than that of the core semiconductor nanocrystal. For semiconductor nanocrystal cores that emit energy in the visible (e.g., Si, Ge, GaP) or near-infrared (e.g., InP, InN, PbS, PbSe), a material that has a band energy in the ultraviolet regions can be used. Examples thereof include ZnS, GaN, and magnesium chalcogenides (e.g., MgS, MgSe, and MgTe).

For a semiconductor nanocrystal core that emits energy in the near-infrared regions, a material that has a band energy in the visible regions can also be used.

In the invention, especially preferred semiconductor material is $SiO_2$ or ZnS.

The entire core surface is not necessarily required to be covered with the shell in the invention as long as the core whose surface is partially exposed causes no adverse effect.

(Manufacturing Method of Fluorescent Semiconductor Microparticles)

As a manufacturing method of the fluorescent semiconductor microparticles in the invention, conventional known methods can be used.

As the manufacturing methods according to a liquid phase method, there are a co-precipitation method, a sol-gel method, a uniform precipitation method, and a reduction method, which are precipitation methods. In addition, a reverse micelle method and a super critical water thermal synthesis method is an excellent method in preparing nanoparticles (see, for example, Japanese Patent O.P.I. Publication Nos. 2002-32246, 2005-239775, 10-310770 and 2000-104058).

As the manufacturing methods according to a gas phase method, the following methods are used: (a) a method in which a semiconductor material is evaporated in a first high temperature plasma generated between opposed electrodes and then passed in a second high temperature plasma generated by non-electrode discharge under reduced pressure (see, for example, Japanese Patent O.P.I. Publication No. 6-279015); (b) a method in which nanoparticles are separated or removed from an anode composed of a semiconductor material (see, for example, Japanese Translation of PCT International Application Publication No. 2003-515459); and (c) a laser ablation method (see, for example, Japanese Patent O.P.I. Publication No. 2004-356163). Further, a method is preferably used also, in which powder containing the particles is obtained by a gas phase reaction of a material gas under reduced pressure.

As a manufacturing method of the fluorescent semiconductor microparticles in the invention, the liquid phase method is especially preferred.

In order to secure uniformity of the particle size or emission intensity of the fluorescent semiconductor microparticles in the invention, it is required that purity of raw materials, synthesis concentration, synthesis temperature and time, and annealing temperature and time after the particle formation are optimized to obtain fluorescent semiconductor microparticles with high crystallinity and minimized lattice defects.

(Surface Modification of Fluorescent Semiconductor Microparticles)

In order to use the fluorescent semiconductor micraparticles in the invention as a labeling agent applicable to a biological substance, the surface of the fluorescent semiconductor microparticles is required to be modified with a surface-modifying compound.

Each of the fluorescent semiconductor microparticles having a different particle size constituting the fluorescent semiconductor microparticle assembly is preferably surface-modified with a different surface modifying compound suitable for a different biological target.

The surface modifying compound is preferably one having at least one functional group and at least one group to be associated with fluorescent semiconductor microparticles. The latter group is a group capable of being absorbed onto the hydrophobic fluorescent semiconductor microparticles, and the other group is a group having affinity to a bio-molecule and capable of being associated with it. Various linkers, through which the surface modifying compounds combine with each other, can be used.

A group with which the fluorescent semiconductor microparticles combine may be any functional group with which the semiconductor materials for forming the shell or core as described above combine. Accordingly, a preferred functional group suitable for the composition of the shell or the core is preferably selected. In the invention, a thiol group is especially preferred as such a functional group.

The functional groups combining with the bio-material include a carboxyl group, an amino group, a phosphonic acid group, and a sulfonic acid group.

Herein, "bio-material" refers to cells, DNA, RNA, oligonucleotides, proteins, antibody, antigen, endoplasmic reticulum, nuclei and Golgi body, etc.

As a method for associating the surface modifying compound with the fluorescent semiconductor microparticles, a compound having a mercapto group is associated with the fluorescent semiconductor microparticles through the mercapto group, adjusted to pH suitable for the surface modification. An aldehyde group, an amino group or a carboxyl group, which is incorporated into the free end of the surface modifying compound molecule, can be associated with an amino group or a carboxyl group of a biological substance to form a peptide bond The similar bond as above can be formed in DNA or oligonucleotide which is incorporated with an amino group, an aldehyde group or a carboxyl group.

The surface-modified fluorescent semiconductor microparticles can be prepared according to a method described in, e.g., Dabbousi et al. (1997) J. Phys. Chem. B 101:9463, Hines et al. (1996) J. Phys. Chem. 100: 468-471, Peng et al. (1997) J. Am. Chem. Soc. 119:7019-7029, and Kuno et al. (1997) J. Phys. Chem. 106:9869.

(Fluorescent Labeling Agent Assembly for Biological Substance and Bioimaging Method Using It)

The fluorescent semiconductor microparticle assembly of the invention can be applied as a fluorescent labeling agent for a biological substance based on the reasons as described below. Further, the fluorescent labeling agent in the invention for a biological substance is added to living cells or living organisms having target (trace) substances to conjugate with or adsorb on, the target (trace) substances. When the resulting conjugate or adsorbed material is irradiated with an excitation light having a specific wavelength, then an emission light having a specific wavelength is emitted from the fluorescent semiconductor microparticles according to the irradiated excitation light is detected, whereby fluorescent dynamic imaging of the target (trace) substances described above can be carried out. That is, the fluorescent semiconductor microparticle assembly for a biological substance of the invention can be applied to a bioimaging method (a technical approach for visualizing a biological molecule constituting a biological substance or its dynamic phenomenon).

Further, as a biological substance analysis method, a multi flow cytometry of a biological substance can be carried out employing polymer beads, in which the fluorescent semiconductor microparticle assembly of the invention is buried.

Next, the fluorescent labeling agent for a biological substance and the related technique will be explained in detail.

The surface-modified fluorescent semiconductor microparticles (hereinafter also referred to as surface-modified semiconductor microparticles) in the invention can be conjugated through the functional group of the surface modification compound to an affinity molecule that serves as a first member of a binding pair. For Example, ionizable groups present within the hydrophilic regions of the surface modification compound may provide the means for linkage to the affinity molecule.

Suitable methods of conjugating molecules and molecular segments to affinity molecules are described, for example, in Hermanson, Bioconjugate Techniques (Academic Press, NY, 1996).

"Conjugates" of such surface-modified semiconductor microparticles by virtue of the affinity molecule can be used to detect the presence and/or quantity of biological substances, i.e., biological compounds and chemical compounds, interactions in biological systems, biological processes, alterations in biological processes, or alterations in the structure of biological compounds. That is, the affinity molecule, when linked to the surface-modified semiconductor microparticles, can interact with a biological target that serves as the second member of the binding pair, in order to detect biological processes or reactions, or to alter biological molecules or processes.

Preferably, the interaction of the affinity molecule and the biological target involves specific binding, and can involve covalent, non-covalent, hydrophobic, hydrophilic, van der Waal's, or magnetic interaction. Further, the affinity molecule can physically interact with the biological target.

The affinity molecule associated with the surface-modified semiconductor microparticles can be naturally occurring or chemically synthesized, and can be selected to have a desired physical, chemical or biological property.

Such properties include covalent and non-covalent association with proteins, nucleic acids, signaling molecules, prokaryotic or eukaryotic cells, viruses, subcellular organelles and any other biological compounds, but are not limited thereto.

Other properties of such molecules include, the ability to affect a biological process (e.g., cell cycle, blood coagulation, cell death, transcription, translation, signal transduction, DNA damage or cleavage, production of radicals, scavenging radicals, etc.), and the ability to alter the structure of a biological compound (e.g., crosslinking, proteolytic cleavage, radical damage, etc.), but are not limited thereto.

In a preferred embodiment, the surface-modified semiconductor microparticle conjugate is comprised of a semiconductive microparticle that emits light at a tunable wavelength and is associated with a nucleic acid. The association can be direct or indirect. The nucleic acid can be any ribonucleic acid, deoxyribonucleic acid, dideoxyribonucleic acid, or any derivatives and combinations thereof. The nucleic acid can also be oligonucleotides of any length. The oligonucleotides can be single-stranded, double-stranded, triple-stranded or higher order configurations (e.g., Holliday junctions, circular single-stranded DNA, circular double-stranded DNA, DNA cubes (see Seeman (1998) Ann. Rev. Biophys. Biomol. Struct. 27:225-248)).

The preferred uses of the semiconductor microparticle conjugate in the invention are detecting and/or quantitating of nucleic acids as follows: (a) viral nucleic acids; (b) bacterial nucleic acids; and (c) numerous human sequences of interest, e.g., single nucleotide polymorphisms. Without limiting the scope of the present invention, the fluorescent semiconductor microparticle conjugates can comprise fluorescent semiconductor microparticle associated with individual nucleotides, deoxynucleotides, dideoxynucleotides or any derivatives and combinations thereof and used in DNA polymerization reactions such as DNA sequencing, reverse transcription of RNA into DNA, and polymerase chain reactions (PCR).

Nucleotides also include monophosphate, diphosphate and triphosphates and cyclic derivatives such as cyclic adenine monophosphate (cAMP).

Other uses of the fluorescent semiconductor microparticles conjugated to nucleic acids include fluorescence in situ hybridization (FISH). In this preferred embodiment, the fluorescent semiconductor microparticles are conjugated to oligonucleotides designed to hybridize to a specific sequence in vivo. Upon hybridization, the fluorescent semiconductor microparticle tags are used to visualize the location of the desired DNA sequence in a cell. For example, the cellular location of a gene whose DNA sequence is partially or completely known can be determined using FISH.

Any DNA or RNA whose sequence is partially or completely known can be visually targeted using FISH. For example without limiting the scope of the present invention, messenger RNA (mRNA), DNA telomeres, other highly repeated DNA sequences, and other non-coding DNA sequencing can be targeted by FISH.

The fluorescent semiconductor microparticle conjugate may also comprise a surface-modified fluorescent semiconductor microparticle as provided herein in association with a molecule or reagent for detection of biological compounds such as enzymes, enzyme substrates, enzyme inhibitors, cellular organelles, lipids, phospholipids, fatty acids, sterols, cell membranes, molecules involved in signal transduction, receptors and ion channels.

The conjugate also can be used to detect cell morphology and fluid flow; cell viability, proliferation and function; endocytosis and exocytosis (Betz et al. (1996) Curr. Opin. Neurobiol. 6(3):365-71); and reactive oxygen species (e.g., superoxide, nitric oxide, hydroxyl radicals, oxygen radicals). In addition, the conjugate can be used to detect hydrophobic or hydrophilic regions of biological systems.

Conjugates of the fluorescent labeling agents for a biological substance (the fluorescent semiconductor microparticle conjugates) also find utility in numerous other biological and non-biological applications where luminescent markers, particularly fluorescent markers, are typically used. See, for example, Haugland, R. P. Handbook of Fluorescent Probes and Research Chemicals (Molecular Probes, Eugene, Oreg. Sixth Ed. 1996; Website, www.probes.com.).

Examples of areas in which the fluorescent labeling agents in the invention for a biological substance are useful include fluorescence immunocytochemistry, fluorescence microscopy, DNA sequence analysis, fluorescence in situ hybridization (FISH), fluorescence resonance energy transfer (FRET), flow cytometry (Fluorescence Activated Cell Sorter; FACS) and diagnostic assays for biological systems, but are not limited thereto.

For further discussion concerning the utility of nanocrystal conjugates in the aforementioned areas, see International Patent Publication No. WO 00/17642 to Bawendi et al.

With respect to the polymer beads, Japanese Translation of PCT International Application Publication Nos. 2006-512929 and 2005-518402, and Japanese Patent O.P.I. Publication Nos. 2006-131771 are referred to.

As is described above, the present invention can be applied to immunostaining or cell observation employing a fixed cell, real-time tracking of receptor-ligand (a low molecular weight compound, a chemical) interaction, and one molecule fluorescence imaging.

EXAMPLES

The invention will be explained in detail employing examples, but the invention is by no means limited to these.

Example 1

(Preparation of Fluorescent Semiconductor Microparticle ($Si/SiO_2$.Core/Shell Particle) Assembly)

Fluorescent semiconductor microparticles, composed of Si (hereinafter also referred to as Si semiconductor microparticles or Si core particles), are prepared by dissolving thermally treated $SiO_x$ (x-1.999) in a hydrofluoric acid solution. Firstly, an $SiO_x$ (x-1.999) film formed onto a silicone wafer via plasma CVD was annealed at 1,000° C. for two hours under an inert gas atmosphere, whereby Si semiconductor microparticles (crystals) were deposited in the $SiO_2$ film. Subsequently, the resulting silicone wafer was treated at room temperature with a 1% aqueous hydrofluoric acid solution to remove the $SiO_2$ film, whereby Si crystals with a size of several nm, which aggregated on the surface of the solution, were obtained. According to the above hydrofluoric acid treatment, the dangling bond (being a non-bonding chemical bond) of the Si atoms of the crystal surface is terminated by hydrogen, whereby Si core particles are stabilized. Thereafter, the surface of the resulting Si semiconductor microparticle (crystals) are subjected to natural oxidation under an oxygen atmosphere, or to thermal oxidation whereby a shell layer composed of $SiO_2$ was formed on the periphery of the core composed of Si crystals.

The particle size of the resulting particles was 2.5 nm (core), measured employing a Zetasizer produced by SIS-MECS Co., Ltd.

Si core particles having a different particle size were prepared in the same manner as above, provided that the annealing temperature or time was changed, or conditions under which hydrofluoric acid solution were controlled.

Si core particles with a larger size were obtained by elevation of the annealing temperature and shortening of the annealing time.

Thus, core/shell particles containing core particles having a particle size of 3.0 nm, 3.4 nm, 3.8 nm and 4.4 nm were obtained.

(Comparative Particles 1: Preparation of $CdSe/SiO_2$.Core/Shell Particles)

In an eggplant flask were placed 0.14 g of cadmium acetate and 5.0 g of trioctylphosphine oxide (TOPO). After the interior of the flask was filled with argon, the mixture solution was heated to an intended temperature (150 to 250° C.). Then, 1.44 $cm^3$ of a selenium tri-n-octylphosphine oxide solution having a Se concentration of 25 $mg/cm^3$ were poured in the mixture solution with vigorous stirring, and further stirred for additional one hour to obtain a TOPO stabilized CdSe (hereinafter referred to as TOPO/CdSe). When TOPO/CdSe was prepared at 290° C., 250° C., 200° C., and 150° C., the standstill time being adjusted at each temperature, the resulting CdSe nanoparticles had rising wavelengths in the absorption spectra of 660 nm, 610 nm, 580 nm and 550 nm, and particle sizes of 7.5 nm, 6.2 nm, 5.5 nm and 4.5 nm, respectively. Employing the TOPO/CdSe powder, the CdSe nanoparticles were surface-modified with 3-mercaptopropyltrimethoxysilane and subjected to hydrolysis to obtain CdSe core/silica shell particles (hereinafter referred to as CdSe/$SiO_2$) in which a silica thin film was formed on the surface of the particles. The resulting CdSe core/silica shell particles were subjected to monochromatic light (560 nm) exposure in the photo-solubilizing solution, where cadmium selenide (CdSe) nanoparticles within the core/shell structure were subjected to size selection photo-etching to reduce the particle size to about 3.5 nm, whereby a fluorescent material composed of the core/shell structure was obtained.
(Comparative Particles 2: Preparation of CdSe/ZnS.Core/Shell Particles)

In an eggplant flask were placed 0.14 g of cadmium acetate and 5.0 g of trioctylphosphine oxide (TOPO). After the interior of the flask was filled with argon, the mixture solution was heated to an intended temperature (150 to 250° C.). Then, 1.44 cm$^3$ of a selenium tri-n-octylphosphine oxide solution having a Se concentration of 25 mg/cm$^3$ were poured in the mixture solution with vigorous stirring, and further stirred for additional one hour to obtain a TOPO stabilized CdSe (hereinafter referred to as TOPO/CdSe). Particles having the same particle size as Comparative Particles 1 were obtained.

The resulting Cd/Se core particles were dispersed in pyridine and maintained at 100° C. Separately, $Zn(C_2H_5)_2$, $((CH_3)_3Si)_2S$ and $P(C_4H_9)_3$ were slowly mixed under argon atmosphere.

The mixture was dropwise added to the pyridine dispersion The resulting mixture dispersion was slowly stirred for 30 minutes while appropriately controlling the temperature and maintaining at a constant pH (at a pH of 8.5 at 25° C.). The resulting dispersion was subjected to centrifuge to collect the precipitated particles. CdSe and ZnS were confirmed from elemental analysis of the precipitates, and it proved that the CdS surface was covered with ZnS according to XSP analysis.

The particle size of the core and core/shell particles as prepared above was measured through Zetasizer ZS produced by SISMECS Co., Ltd.
(Introduction of Modification Functional Group)

It is necessary that when biological substances are labeled with the above-obtained fluorescent semiconductor microparticles, a functional group, through which the microparticles and the biological substances are linked to each other, is introduced in either or both of the microparticles and the biological substances. The introduction was carried out as follows.
(Introduction of Modification Functional Group into Si/SiO$_2$ Core/Shell Particles)

A carboxyl group was introduced into Si fluorescent semiconductor microparticles employing a mercapto group (SH group) bonding. Firstly, the Si fluorescent semiconductor microparticles were dispersed in a 30% hydrogen peroxide aqueous solution for 10 minutes to hydroxidize the crystal surface thereof. Subsequently, the solvent of the dispersion was replaced with toluene, and mercaptopropyltriethoxysilne was added in an amount of 2% of the toluene. Herein, SiO$_2$ on the surface of the Si fluorescent semiconductor microparticles was silanized and simultaneously subjected to introduction of a mercapto group. Successively, the resulting dispersion, after the solvent was replaced with pure water, was added with a buffer salt, and further with an appropriate amount of 11-mercaptoundecanoic acid having a mercapto group at one end thereof, and stirred for three hours, whereby 11-mercaptoundecanoic acid was associated with the SiSi fluorescent semiconductor microparticles. This is an example in which a modification group to be associated with a biological substance was introduced in the particles. The resulting samples were designated as Marker A (Markers A-1, A-2, A-3, A-4 and A-5).
(Introduction of Modification Functional Group into CdSe/SiO$_2$ Core/Shell Particles)

In the same manner as in Marker A, 11-mercaptoundecanoic acid was associated with the surface of the particles, whereby a carboxyl group was introduced in the particle surface. The resulting samples were designated as Markers B-1, B-2, B-3, B-4 and B-5.

(Introduction of Modification Functional Group into CdSe/ZnS Core/Shell Particles)

The CdSe/ZnS core/shell particles obtained above were dispersed in a buffer salt solution, then added with an appropriate amount of 11-mercaptoundecanoic acid, and stirred at an appropriate temperature for two hours to associate the mercapto group with the particle surface, whereby a carboxyl group was introduced in the particle surface. The resulting samples were designated as Markers C-1, C-2, C-3, C-4 and C-5.
<Evaluation of Emission Intensity>

Fluorescence intensity with respect to each Marker was determined according to a fluorescence spectrometer FP-6500 (produced by Nippon Bunko Co.), employing excitation light (405 nm). The fluorescence intensity was represented in terms of a value relative to fluorescence intensity of Marker A set at 100. The results are shown in Table 1.
<Labeling of Cell, Dyeing and Analysis>

Vero cell was labeled with each marker obtained above, which had been mixed with sheep serum albumin (SSA) in the same concentration, and incubated at 37° C. for two hours, subjected to trypsin treatment, re-suspended in the DMEM added with a 5% FBS, reseeded in the same glass bottom dish, and further incubated at 37° C. overnight. The resulting cell sample was fixed with a 4% formalin solution, and the nucleus thereof was dyed with DAPI. Fluorescence of the dyed cell sample was observed employing a confocal laser scan microscope (405 nm excitation light).

Evaluation of the fluorescence observation was carried out as follows. Whether simultaneous multi-color analysis can be carried out was examined in view of color discrimination property. That is, discrimination of all colors, uniformity of color area, and uniformity of fluorescence intensity were evaluated. The results are shown in Tables 1 through 3.

TABLE 1

(Inventive)

| Markers | Core Particle Size (nm) | Emission Intensity (Relative Value) | Standard Deviation (%) | a) |
|---|---|---|---|---|
| A-1 | 2.5 | 100 | 10 | b) |
| A-2 | 3.0 | 103 | 10 | |
| A-3 | 3.4 | 97 | 11 | |
| A-4 | 3.8 | 102 | 10 | |
| A-5 | 4.4 | 105 | 12 | | a) Multicolor Observation Results
b) Five different colors are clearly discriminated. The emission areas of the five different colors are uniform. The emission intensities are uniform. Imaging, which is sufficient to carry out simultaneous analysis of the five different colors, is provided.

TABLE 2

(Comparative)

| Markers | Core Particle Size (nm) | Emission Intensity (Relative Value) | Standard Deviation (%) | a) |
|---|---|---|---|---|
| B-1 | 3.5 | 100 | 20 | c) |
| B-2 | 4.5 | 118 | 3 | |
| B-3 | 5.5 | 150 | 35 | |
| B-4 | 6.2 | 140 | 20 | |
| B-5 | 7.5 | 90 | 35 | | a) Multicolor Observation Results
c) Five different colors are not sufficiently discriminated. In B-2 and B-5, some colors are healed and unclear. The emission areas vary. B-3 exhibits high emission intensity, but others poor emission intensity. Imaging, which is insufficient to carry out simultaneous analysis of the five different colors, is provided.

TABLE 3

(Comparative)

| Markers | Core Particle Size (nm) | Emission Intensity (Relative Value) | Standard Deviation (%) | |
|---|---|---|---|---|
| C-1 | 3.5 | 100 | 23 | d) |
| C-2 | 4.5 | 125 | 5 | |
| C-3 | 5.5 | 160 | 40 | |
| C-4 | 6.2 | 150 | 33 | |
| C-5 | 7.5 | 80 | 40 | | a) Multicolor Observation Results
d) Five different colors are not sufficiently discriminated. In C-2 and C-5, some colors are healed and unclear. The emission areas vary. C-3 exhibits high emission intensity, but others poor emission intensity. Imaging, which is insufficient to carry out simultaneous analysis of the five different colors, is provided.

As is apparent from Tables 1 through 3, the reason that there is difference in emission intensities among different colors is due to the fact that the toe region of spectra of particles emitting a color light with higher emission intensity extends to the spectral region of particles emitting other color lights, thereby lowering the color discrimination.

As is apparent from the above, the fluorescent semiconductor microparticle assembly, comprising at least three kinds of fluorescent semiconductor microparticles with a different particle size and a different emission maximum wavelength in the emission spectra, wherein a standard deviation of emission intensity of each of the fluorescent semiconductor microparticles is not more than 15%, can provide a clear and simultaneous multicolor bio-imaging method of a biological substance.

The invention claimed is:

1. A fluorescent semiconductor microparticle assembly comprising at least three types of fluorescent semiconductor microparticles with an average particle size of from 1 to 10 nm, having the same chemical composition, each of the at least three types of fluorescent semiconductor microparticles having a different average particle size and a different emission maximum wavelength in the emission spectra from the other, wherein a standard deviation of emission intensity in each of the at least three types of fluorescent semiconductor microparticles is not more than 15%.

2. The fluorescent semiconductor microparticle assembly of claim 1, wherein the emission maximum wavelength in the emission spectra is in the range of from 380 to 800 nm.

3. The fluorescent semiconductor microparticle assembly of claim 1, wherein the at least three types of fluorescent semiconductor microparticles are irradiated with one or a single excitation light to emit light.

4. A method of manufacturing a fluorescent semiconductor microparticle assembly according to a liquid phase method, comprising:

assembling at least three types of fluorescent semiconductor microparticles with an average particle size of from 1 to 10 nm, having the same chemical composition, each of the at least three types of fluorescent semiconductor microparticles having a different average particle size and a different emission maximum wavelength in the emission spectra from the other, wherein a standard deviation of emission intensity in each of the at least three types of fluorescent semiconductor microparticles is not more than 15%.

* * * * *